United States Patent [19]

Jackisch

[11] 4,343,956
[45] Aug. 10, 1982

[54] STABILIZATION DIBROMOSTYRENE

[75] Inventor: Philip F. Jackisch, Royal Oak, Mich.

[73] Assignee: Ethyl Corporation, Richmond, Va.

[21] Appl. No.: 274,829

[22] Filed: Jun. 18, 1981

Related U.S. Application Data

[63] Continuation of Ser. No. 130,118, Mar. 13, 1980, abandoned.

[51] Int. Cl.³ .............................................. C07C 17/42
[52] U.S. Cl. .................................. 570/105; 570/111; 570/103; 252/403
[58] Field of Search ............... 570/103, 105, 111, 102; 252/403

[56] References Cited

U.S. PATENT DOCUMENTS 2,181,102  11/1939  Stoesser et al. .................. 260/650 R
2,295,077   9/1942  Dreisbach et al. ............. 260/650 R
4,104,196   8/1978  Zaffarow ........................... 252/403
4,177,110  12/1979  Watson .................................. 585/5
4,182,658   1/1980  Watson .................................. 203/9

FOREIGN PATENT DOCUMENTS 1230979  5/1971  United Kingdom ............ 260/650 R

OTHER PUBLICATIONS

Quarterly J. of Pharmacy, vol. 16, pp. 232–243 (1943).

Primary Examiner—Delbert E. Gantz
Assistant Examiner—Joseph A. Boska
Attorney, Agent, or Firm—Donald L. Johnson; Joseph D. Odenweller; John F. Hunt

[57] ABSTRACT

Dibromostyrene has a marked tendency to polymerize on storage. The induction period can be lengthened with the use of a stabilizing quantity of n-propylgallate. The induction period can be markedly prolonged when the gallate ester is admixed with phenothiazine, N,N,N',N'-tetramethyl-p-phenylenediamine, or 4-tert-butyl catechol.

4 Claims, 1 Drawing Figure

A = induction period
B = initial rate (°C/min.)
C = time to temperature maximum
D = temperature maximum Representative Differential Thermal
Analysis Curve of Polymerization

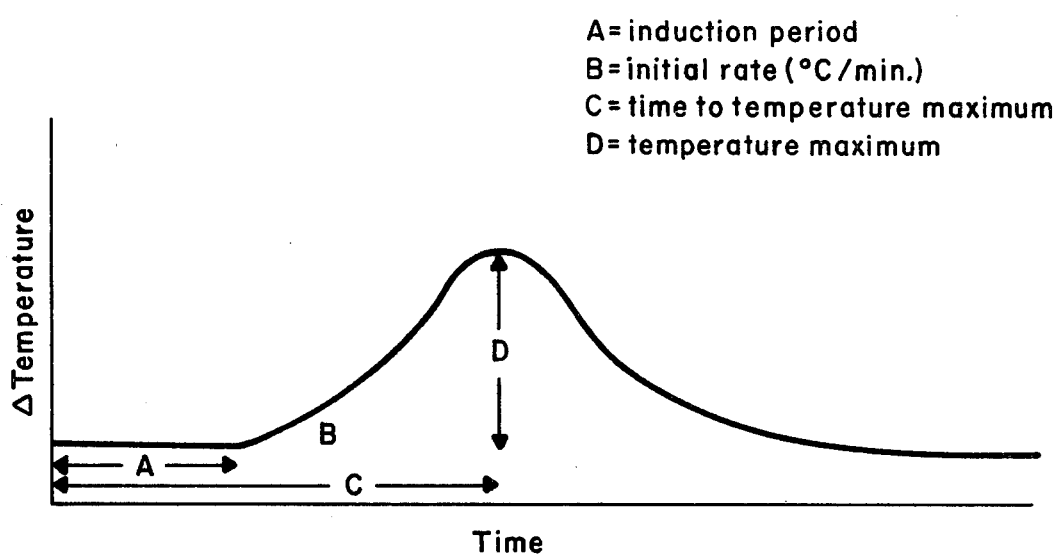
Representative Differential Thermal Analysis Curve of Polymerization

STABILIZATION DIBROMOSTYRENE

This application is a continuation of application Ser. No. 130,118, filed Mar. 13, 1980, now abandoned.

BACKGROUND OF THE INVENTION

Dibromostyrene, which has been suggested as a flame retardant monomer, has a considerable tendency to undergo polymerization during storage. This polymerization tendency is greater than with styrene itself. It has been suggested in British Pat. No. 1,230,979, that dibromostyrene be stabilized with picric acid or a mixture of picric acid and (i) a quinone such as hydroquinone or benzoquinone, or (ii) a phenol such as tert-butyl catechol.

DESCRIPTION OF THE DRAWING

The drawing shows a representation of a differential thermal analysis (DTA) curve obtained when the polymerization of dibromostyrene with an inhibitor is followed by DTA using the apparatus and procedure described herein. As shown, the value for (A) indicates how long the induction period before the polymerization ensues, while the value for (C) indicates the time for the polymerization to reach its maximum. The slope of the curve at (B) after the terminus of (A) is an indication of the polymerization rate, while the height of (C) gives the temperature maximum reached.

Without a polymerization inhibitor, the period indicated by (A) is non-existent or very short. With a polymerization retardant, it makes the slope of the line at (B) less steep and diminishes the height of (D). The average polymerization rate in °C. per unit time can be calculated rom the slope of the line connecting the end of (A) with the maximum of the curve; i.e. where the curve is intercepted by the height (D).

SUMMARY OF THE INVENTION

This invention comprises the discovery that undesired polymerization of dibromostyrene during storage is reduced if the dibromostyrene is intimately mixed with a lower alkyl gallate wherein the alkyl group is from one to five or more carbon atoms. Because propylgallate is an additive of commerce, a preferred embodiment of the invention comprises use of that substance as a polymerization stabilizer.

This invention also comprises the discovery that a gallate as discussed above can be efficaciously admixed with another substance and the mixture used as a stabiling composition. Preferably, the other substance is phenothiazine, N,N,N',N'-tetramethyl-p-phenylene diamine, tert-butyl catechol or mixture thereof.

This invention also comprises as compositions of matter, stabilizing mixtures for dibromostyrene of a gallate such as n-propylgallate and one or more of the compounds mentioned above, viz, phenothiazine, N,N,N',N'-tetramethyl-p-phenylenediamine or 4-tert-butyl catechol.

DESCRIPTION OF PREFERRED EMBODIMENTS

This invention can be used with dibromostyrene (which is usually mostly 3,4- or 2,4-ar-dibromostyrene) prepared by any method. For example, it can be used with dibromostyrene made by a process disclosed in my copending application entitled "Preparation of Dibromostyrene" and filed on the same day as this application. Better results are achieved if the dibromostyrene contains a minimum or low level of β-bromoethyldibromobenzene impurity and a low level of tribromostyrene impurity. Thus for β-bromoethyldibromobenzene, it is preferred that it be present in an amount less than about 0.1 weight percent, and for tribromostyrene, it is preferred that the level be less than about 2 weight percent. As shown below, the invention can be used to stabilize dibromostyrene containing about 8-9 weight percent tribromostyrene, but greater increases in inhibition time via this invention will occur if the amount of tribromostyrene is less.

The gallate ester which is employed in this invention as an inhibitor is preferably a lower alkyl ester of, say, seven or less, carbon atoms, preferably 1–5 and most preferably 3. A stabilizing quantity of such gallate ester is employed, i.e. an amount of ester which gives an increase in induction time by the test procedure described in the example given below. Generally, the amount of gallate used is from about 20 to about 2000 ppm with greater or lesser amounts being used if desired.

As exemplified below, it has been discovered that the induction period can be markedly enhanced by admixing propyl gallate with a compound selected from the class consisting of phenothiazine, N,N,N',N'-tetramethyl-p-phenylenediamine, and 4-tert-butyl catechol. Generally, when these compounds are used in conjunction with the gallate, they are employed in an amount from about 20 to about 2000 ppm, more preferably from about 100 to about 600 ppm. Greater or lesser amounts can be used if desired. The good results when such mixtures are used suggest that compounds related to the above-named compounds can be admixed with the gallate. For example, it is suggested that an alkyl substituted phenothiazine such as a methylphenothiazine, or a dimethylphenothiazine can be used, or N,N,-dimethylphenylenediamine, or a phenylenediamine or diphenylenediamine wherein the N atoms are substituted with ethyl rather than methyl groups. Likewise, it is suggested that the 4-tert-butyl catechol be substituted with a compound such as those suggested by British Pat. No. 1,230,979, supra, to be used with picric acid.

EXAMPLE 1

A differential thermal analysis apparatus was constructed to measure the heat of polymerization of stored monomer samples. Two thermopiles were constructed (originally with 6 thermocouples each but more recently with 5) with iron-Constantin junctions. Sample containers consisted of 18 ml wide-mouthed bottles with caps drilled with a hole through which was fitted a piece of glass tubing sealed at the bottom end to form a thermowell. The glass tubes were 8 mm in outside diameter and 90 mm long and were filled with 5 drops of Dow Corning's No. 200 Silicone Oil to help in heat transfer. The thermopiles were inserted into the thermowells of two cells, one containing an inert fluid (originally m-dibromobenzene but more recently Dow Corning No. 200 Silicone Oil), and the other approximately 15 g (9 ml) of dibromostyrene or an equal volume of bromostyrene or styrene. The sample and reference cells were placed in a wooden holder in a Blue M, Stabil-Therm Poweromatic 70 oven. The oven temperature was measured with a Doric Trendicator 400 A type K/°C. digital pyrometer connected to a thermocouple with its end in the wooden cell holder. The temperature differential between the reference cell and the monomer-containing cell was recorded on a Houston Instruments OmniScribe recorder at either 1 millivolt or 10 millivolts full scale (equal to 4.8 or 48 degrees C.).

The dibromostyrene used had 8.7 percent tribromostyrene and 1.1 percent monobromostyrene.

The results were as follows:

| Inhibitor | Temperature 75° C. | | | | |
|---|---|---|---|---|---|
| | Induction Period | Initial Poly. Rate | Average Poly. Rate | Time of Max. Rate | Temp. Max. |
| 400 ppm each | | | | | |
| 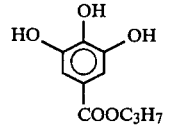 | 2.1 | 0.40 | 0.23 | 10.9 | 2.0 |
| Phenothiazine and propyl gallate | 31.1 hr. | 0.065° hr. | 0.50° hr | 35.7 hr | 2.3° |
| 4-t-butylcatechol and propyl gallate | 5.4 | 0.35 | 0.12 | 18.1 | 1.6 |
| 4-Methylcatechol and propyl gallate | 1.4 | 2.9 | 0.49 | 4.1 | 1.3 |
| N,N,N',N'-tetramethyl-p-phenylenediamine and propyl gallate | 76.6 | 0.029 | 0.11 | 91.6 | 1.6 |

The above results suggest use of propyl gallate in an amount of from about 20 to about 2000 ppm alone or together with from about 20 to about 2000, preferably from about 100 to about 600 ppm of phenothiazine, 4-tert-butyl catechol or N,N,N',N'-tetramethyl-p-phenylenediamine.

The above results also indicate that the stabilizers and stabilizer mixtures of this invention can be used with dibromostyrene containing less than 0.1 weight percent β-bromoethyldibromobenzene, and less than 2 weight percent tribromostyrene.

The process of this invention is especially useful in protecting dibromostyrene from unwanted polymerization during storage. Thus, this invention is particularly directed to prevention of unwanted polymerization at temperatures below about 35°–38° C. Test temperatures such as 75° C. can be utilized as above for acceleration of test time periods.

Because of the long induction period, the propyl gallate, N,N,N',N'-tetramethyl-p-phenylenediamine system described in the above test results is highly preferred.

For a comparison, the results described in the above table can be contrasted with the following results obtained when no inhibitor was employed:

| | |
|---|---|
| Induction Period | 0 hr. |
| Initial Polymerization Rate | 3.8°/hr. |
| Average Polymerization Rate | 4.4°/hr. |
| Time of Maximum Rate | 1.5/hr. |
| Temperature maximum | 6.3° |

I claim:

1. Dibromostyrene stabilized with a polymerization inhibiting quantity of a lower alkyl ester of gallic acid and a synergistic quantity of N,N,N',N'-tetramethyl-p-phenylenediamine.

2. A composition of claim 1 wherein said ester is propyl gallate.

3. A composition of claim 2 wherein said propyl gallate is present in an amount of from about 20 to about 2000 ppm.

4. As a composition of matter, a mixture for stabilizing dibromostyrene comprising a lower alkyl gallate and an additional stabilizing compound N,N,N',N'-tetramethyl-p-phenylenediamine where the ratio of said gallate to said additional compound is from about 0.01 to about 10 to 1.

* * * * *

UNITED STATES PATENT AND TRADEMARK OFFICE
CERTIFICATE OF CORRECTION

PATENT NO. : 4,343,956
DATED : August 10, 1982
INVENTOR(S) : Philip F. Jackisch

It is certified that error appears in the above-identified patent and that said Letters Patent are hereby corrected as shown below:

On the Title Page and Column 1,

Title of Invention - "STABILIZATION DIBROMOSTYRENE" should be -- STABILIZATION OF DIBROMOSTYRENE --

Column 2, line 44 - insert the following paragraph:

Generally most phenols do form stable picrates. Examples of these are catechol itself, resorcinol, phloroglucinol and alkyl substituted, particularly t-alkyl substituted, derivatives thereof. Naphthoquinones and anthraquinones are not thought, generally, to form stable picrates but most benzoquinones are, for example dialkyl benzoquinones or chloroanil. Other substituted phenols, for example dinitrophenol, are thought to form stable picrates. Certain quinones or phenols themselves show an inhibiting effect on the polymerization of styrene based monomers particularly on styrene itself and it is particularly desirable to use these. Examples of such quinones and phenols are t-butyl catechol, benzoquinone and hydroquinone.

Signed and Sealed this

Twenty-sixth Day of October 1982

[SEAL]

Attest:

GERALD J. MOSSINGHOFF

Attesting Officer

Commissioner of Patents and Trademarks